(12) United States Patent
Shim et al.

(10) Patent No.: US 7,700,290 B2
(45) Date of Patent: Apr. 20, 2010

(54) METHOD OF MANUFACTURING DNA CHIP

(75) Inventors: Jeo-young Shim, Yongin-si (KR);
Soo-suk Lee, Suwon-si (KR);
Chin-sung Park, Yongin-si (KR);
Kyu-youn Hwang, Incheon-si (KR)

(73) Assignee: Samsung Electronics Co., Ltd. (KR)

( * ) Notice: Subject to any disclaimer, the term of this patent is extended or adjusted under 35 U.S.C. 154(b) by 86 days.

(21) Appl. No.: 11/479,306

(22) Filed: Jun. 30, 2006

(65) Prior Publication Data

US 2007/0003967 A1    Jan. 4, 2007

(30) Foreign Application Priority Data

Jul. 2, 2005    (KR) .................. 10-2005-0059489

(51) Int. Cl.
*C12Q 1/68*    (2006.01)
*C12M 1/00*    (2006.01)
*C12M 3/00*    (2006.01)

(52) U.S. Cl. .................. 435/6; 435/283.1; 435/287.2; 536/23.1; 536/24.3; 257/368

(58) Field of Classification Search .................. 435/6, 435/283.1, 287.2; 536/23.1, 24.3; 257/368
See application file for complete search history.

(56) References Cited

U.S. PATENT DOCUMENTS

| | | | |
|---|---|---|---|
| 4,393,130 | A | 7/1983 | Ho et al. |
| 5,545,531 | A * | 8/1996 | Rava et al. .................. 506/23 |
| 6,733,355 | B2 * | 5/2004 | Hwang et al. .................. 445/24 |
| 2003/0087179 | A1 * | 5/2003 | Iwasaki .................. 430/166 |
| 2003/0096081 | A1 * | 5/2003 | Lavallee et al. .................. 428/138 |
| 2003/0102510 | A1 * | 6/2003 | Lim et al. .................. 257/368 |
| 2004/0238379 | A1 * | 12/2004 | Lindsay et al. .................. 205/792 |

FOREIGN PATENT DOCUMENTS

| | | |
|---|---|---|
| EP | 1161985 | 12/2001 |
| EP | 1541991 | 6/2005 |
| WO | WO03016912 | 2/2003 |

OTHER PUBLICATIONS

Definition of gate electrode, Chemistry Dictionary, p. 1.*
Design and fabrication of microwell array chips for a solution-based, photogenerated acid-catalyzed parallel oligonuclotide DNA synthesis; Onnop Srivannavit, Mayurachat Gulari, Erdogan Gulari, Eric LeProust, Jean Philippe Pellois, Xiaolian Gao, Xiaochuan Zhou; Sensors and Actuators A 116 (2004) 150-160.
Laminated Dry Film Resist for Microengineering Applications; J. Zhu, A.S. Holmes, J. Arnold, R.A. Lawes and P.D. Prewett; Microelectronic Engineering 30 (1996) 365-368.
An Assessment of Thick Dry Photoresist for Wafer Bumping; Pedro Jorge and Michael Topper; XP-002401345; pp. 1-6.
Generation of libraries by print technologies; Eugen Ermantraut, Sefan Wolfl and Hans Peter Saluz; XP-008013540; BioMethods, vol. 10; 1999; pp. 255-264.
Manufacturing of biomolecular Arrays—a technical challenge; XP008013529; Eugene Ermantraut; medgen 11 (1999).
DNA microarrays in medicine: manufacturing techniques and potential applications; Paul Cullen and Stefan Lorkowski; XP-002401344; Ashley Publications Ltd ISSN; 2002; pp. 1783-1794.
Light-directed synthesis of high-density oligonucleotide arrays using semiconductor photoresists; Glenn McCall, Jeff Labadie, Phil Brock, Greg Wallraff, Tiffany Nguyen and William Hinsberg; XP-000775688; Proc Natl. Acad. Sci USA; vol. 93, pp. 13555-13560, Nov. 1996.
European Search Report; EP06013652; Nov. 9, 2006.

* cited by examiner

*Primary Examiner*—Stephen Kapushoc
*Assistant Examiner*—Narayan K Bhat
(74) *Attorney, Agent, or Firm*—Cantor Colburn LLP

(57) ABSTRACT

A method of manufacturing a DNA (deoxyribonucleic acid) chip is provided. The DNA chip has a plurality of transistors formed on a substrate and an organic layer and a DNA probe sequentially stacked on a gate of the transistor. The method includes forming an inter-layer insulation layer on the substrate to cover the transistors, planarizing the inter-layer insulation layer, forming at least two contact holes exposing gate electrodes of the transistors in the inter-layer insulation layer, selectively forming organic layers on the exposed gate electrodes, attaching a first DFR (dry film resist) layer to the upper surface of the inter-layer insulation layer to cover the contact holes, removing a portion of the first DFR layer covering a first contact hole among the contact holes, attaching a first DNA probe to the organic layers in the first contact hole, and removing a remaining portion of the first DFR layer.

7 Claims, 5 Drawing Sheets

METHOD OF MANUFACTURING DNA CHIP

CROSS-REFERENCE TO RELATED PATENT APPLICATION

This application claims the benefit of Korean Patent Application No. 10-2005-0059489, filed on Jul. 2, 2005, in the Korean Intellectual Property Office, the disclosure of which is incorporated herein in its entirety by reference.

BACKGROUND OF THE INVENTION

1. Field of the Invention

The present invention relates to a method of manufacturing a detection device of a semiconductor apparatus, and more particularly, to a method of manufacturing a deoxyribonucleic acid (DNA) chip.

2. Description of the Related Art

Each of human cells has 23 pairs of chromosomes which includes a lot of genes that can make about 100,000 proteins. All human cells are not able to produce about 100,000 proteins, rather, only some of the genes produce necessary proteins. Assuming that about 10,000 genes are involved in producing proteins in cells, a method of detecting such genes will be described below.

DNA information responsible for producing proteins (e.g., three base sequences such as ATT and CGA) is transferred to ribonucleic acid (RNA). RNA including the DNA information is transported to a ribosome allocated outside a nucleus and synthesizes proteins at the ribosome. Therefore, enormous amounts of DNA information can be detected by sorting RNAs synthesized at cells and decoding base sequences of the RNAs. However, with this method, it would take about a day to find out the genetic structure for synthesizing one protein. Thus, it would take about 10,000 days to find out all the genetic structures.

A recently developed DNA chip greatly shortens the time taken to find out a vast amount of cellular genetic information. The DNA chip includes several hundred thousand DNA probes, and enables researchers to simultaneously monitor the activity of several thousand genes and detect defects. Also, a genetic expression activity of producing proteins in response to the activation of a gene can be estimated using the DNA chip.

The basic principle of the DNA chip is the use of DNA having a single stranded helical structure. The cellular RNA structure is changed into a DNA structure by treating the unstable cellular RNA structure to obtain a stable experimental material containing the same genetic information. Since RNA has a single stranded helical structure, the DNA obtained from the RNA in this way has a single stranded helical structure instead of a double stranded helical structure.

For a detection method of a specific gene using the DNA chip, different DNA probes are prepared within about 100,000 wells of the DNA chip. Each of the DNA probes has a single stranded helical structure. When about 10,000 cellular genes (i.e. DNA) to be detected are injected into the wells of the DNA chip, hybridization between the DNA probes and the injected cellular DNA is initiated at about 10,000 wells of the DNA chip. Hence, assuming that base sequences of about 100,000 genes are all discovered, the 10,000 hybridized genes can be identified from the DNA chip, thereby obtaining the desired genetic information. Knowing the base sequences of DNA makes it possible to identify which amino acids are produced, and thus about 10,000 cellular proteins can be identified using the DNA chip.

Although the DNA chip can be manufactured by various methods, a method of attaching previously synthesized DNA probes to a solid substrate and a method of stacking DNA probes on a solid substrate have recently been employed.

In the conventional DNA chip manufacturing methods, DNA probes are synthesized by photolithography, as commonly used in semiconductor device fabrication.

In this method, an organic layer to be hybridized with bases of DNA probes, for instance, a GAPS layer, exists on a glass substrate. A photoresist layer, which is used in a typical semiconductor fabrication process, is first formed on the organic layer for the purpose of attaching a specific DNA probe to a selected portion of the organic layer. Using a photo-mask exposing a portion of the photoresist layer which covers the selected portion of the organic layer, the exposed portion of the photoresist layer is exposed to light. A developing solution is used to develop the photoresist layer, and the photo-exposed portion of the photoresist layer formed on the selected portion of the organic layer is removed. The resulting structure where the photoresist layer remains on the organic layer except for the selected portion is immersed in a solution including a specific base to be hybridized with the selected portion of the organic layer, and then cleaned. As a result, the specific base (i.e. the DNA probe) is attached to the selected portion of the organic layer, which is exposed by the previous developing process. These sequential operations are performed at other regions of the organic layer.

Compared with conventionally employed methods such as Southern blot, Northern blot, mutant detection, and DNA sequencing, the DNA chip manufactured as above can detect more genes with less specimens within a shorter time. However, the photoresist layer adheres well to the organic layer and the DNA probe. Thus, during the developing process, the photoresist layer may not be completely removed from the organic layer or the DNA probe, and may partially remain on the organic layer or the DNA probe, degrading the activation of the organic layer.

SUMMARY OF THE INVENTION

The present invention provides a method of manufacturing a DNA chip, which can prevent degraded activation of an organic layer and a DNA probe while employing a typical photolithography process.

According to an aspect of the present invention, there is provided a method of manufacturing a DNA chip having a plurality of transistors formed on a substrate and an organic layer and a DNA probe sequentially stacked on a gate of the transistor, the method including: forming an inter-layer insulation layer on the substrate to cover the transistors, and planarizing the inter-layer insulation layer; forming at least two contact holes exposing gate electrodes of the transistors in the inter-layer insulation layer; selectively forming organic layers on the exposed gate electrodes; attaching a first DFR (dry film resist) layer to the upper surface of the inter-layer insulation layer to cover the contact holes; removing a portion of the first DFR layer covering a first contact hole among the contact holes; attaching a first DNA probe to the organic layers in the first contact hole; and removing a remaining portion of the first DFR layer.

The method may further include: forming a second DFR layer on the inter-layer insulation layer covering the contact holes; removing a portion of the second DFR layer covering a second contact hole among the contact holes; attaching a second DNA probe to the organic layers in the second contact hole; and removing a remaining portion of the second DFR layer.

The forming of the contact holes and the selectively forming of the organic layers on the gate electrodes may further include: forming a photoresist pattern on the inter-layer insulation layer, the photoresist pattern defining regions where the gate electrodes are formed; etching the inter-layer insulation layer using the photoresist pattern as an etch mask until the gate electrodes are exposed; forming the organic layers on the upper surfaces of the photoresist pattern and the gate electrodes; and removing the photoresist pattern and the organic layer formed on the photoresist pattern.

The organic layers can be GAPS layers. The portion of the first DFR layer may be removed using a developing solution that does not damage the organic layers. The developing solution can be a mild buffer solution. The remaining portion of the first DFR layer may be removed using an organic solution or stripped under a weak base condition.

According to an embodiment of the present invention, an additional apparatus is not necessary since a conventional photolithography process can still be used. An organic layer or a DNA probe does not make direct contact with a photosensitive layer, and thus the photosensitive layer can be completely removed from the organic layer and the DNA probe. Accordingly, degradation of the activation level of the organic layer and the DNA probe can be avoided.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
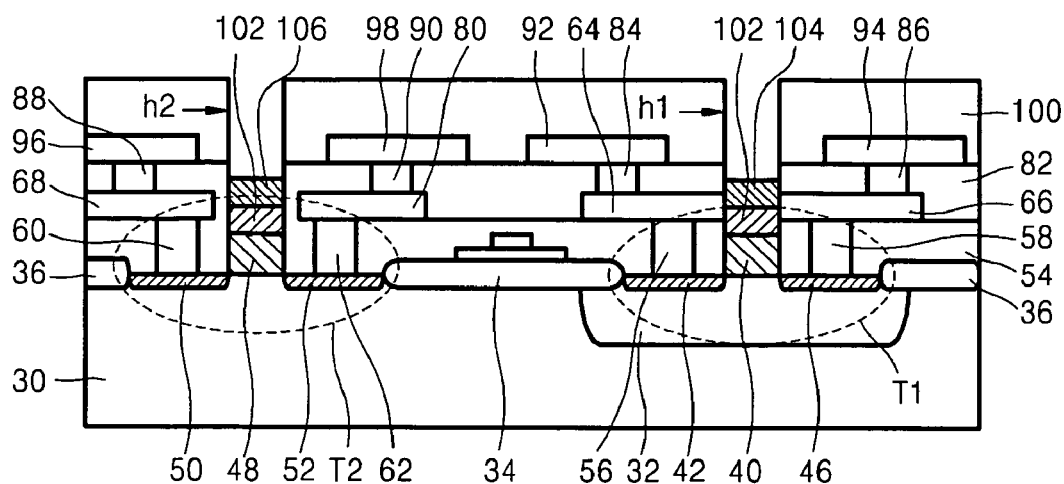
FIG. 1 is a cross-sectional view of a portion of a DNA chip manufactured according to an embodiment of the present invention.

Embodiments of the present invention of a method of manufacturing a DNA chip will now be described in detail with reference to the accompanying drawings. In the drawings, the thicknesses of layers and regions are exaggerated for clarity.

FIG. 1 is a cross-sectional view of a DNA chip manufactured according to an embodiment of the present invention. Although the widths of a first DNA probe 104 and a second DNA probe 106 can be different, they are illustrated as being the same in this drawing for the sake of convenience.

An N-type well 32 is formed in a P-type substrate 30. The substrate 30 also includes device isolation layers 34 and 36, which define the N-type well 32 and a region where an N-channel metal oxide semiconductor (NMOS) transistor is to be formed. A first transistor T1 including a first P-type impurity region 42, a second P-type impurity region 46 and a first gate electrode 40 is formed on the N-type well 32. The first transistor T1 is a biological P-channel MOS (PMOS). A second transistor T2 including a first N-type impurity region 50, a second N-type impurity region 52 and a second gate electrode 48 is formed on a portion of the substrate 30 between the device isolation layers 34 and 36. The second transistor T2 is a biological NMOS. Therefore, the first transistor T1 and the second transistor T2 form a biological complementary MOS (CMOS).

A first inter-layer insulation layer 54 is formed to cover the device isolation layers 34 and 36, the first transistor T1 and the second transistor T2. A first conductive plug 56 and a second conductive plug 58 are connected respectively to the first P-type impurity region 42 and the second P-type impurity region 46 by passing through the first inter-layer insulation layer 54. A third conductive plug 60 and a fourth conductive plug 62 are connected respectively to the first N-type impurity region 50 and the second N-type impurity region 52 by passing through the first inter-layer insulation layer 54. A first pad layer 64 and a second pad layer 66 are formed on the first inter-layer insulation layer 54, covering the first conductive plug 56 and the second conductive plug 58. The first pad layer 64 and the second pad layer 66 are separated from each other. A third pad layer 68 and a fourth pad layer 80 are formed on the first inter-layer insulation layer 54, covering the third conductive plug 60 and the fourth conductive plug 62.

A second inter-layer insulation layer 58 is formed on the first inter-layer insulation layer 54, covering the first to fourth pad layers 64, 66, 68 and 80. The second inter-layer insulation layer 82 can be formed of the same material as the first inter-layer insulation layer 54. A fifth conductive plug 84 and a sixth conductive plug 86 are connected respectively to the first pad layer 64 and the second pad layer 66 by passing through the second inter-layer insulation layer 82. A seventh conductive plug 88 and an eighth conductive plug 90 are connected respectively to the third pad layer 68 and the fourth pad layer 80 by passing through the second inter-layer insulation layer 82. A first electrode layer 92 and a second electrode layer 94 are formed on the second inter-layer insulation layer 82, covering the fifth conductive plug 84 and the sixth conductive plug 86. The first electrode layer 92 and the second electrode layer 94 can respectively be a source electrode and a drain electrode, and are separated from each other. A third electrode layer 96 and a fourth electrode layer 98 are formed on the second inter-layer insulation layer 82, covering the seventh conductive plug 88 and the eighth conductive plug 90. The third electrode layer 96 and the fourth electrode layer 98 can respectively be a source electrode and a drain electrode, and are separated from each other. A third inter-layer insulation layer 100 is formed on the second inter-layer insulation layer 82, covering the first to fourth electrode layers 92, 94, 96 and 98. The third inter-layer insulation layer 100 can include the same material as the first inter-layer insulation layer 54 or the second inter-layer insulation layer 82.

The first to third inter-layer insulation layers 54, 82 and 100 include a first contact hole H1 and a second contact hole H2, respectively exposing the first gate electrode 40 of the first transistor T1 and the second gate electrode 48 of the second transistor T2. A portion of an organic layer 102 and a first DNA probe 104 are sequentially formed on the first gate electrode 40. The organic layer 102 can be a GAPS layer. The first DNA probe 104 includes a specific base. Another portion of the organic layer 102 and a second DNA probe 106 are sequentially formed on the second electrode 48. The second DNA probe can include a different base from that of the first DNA probe.

Figure 2:
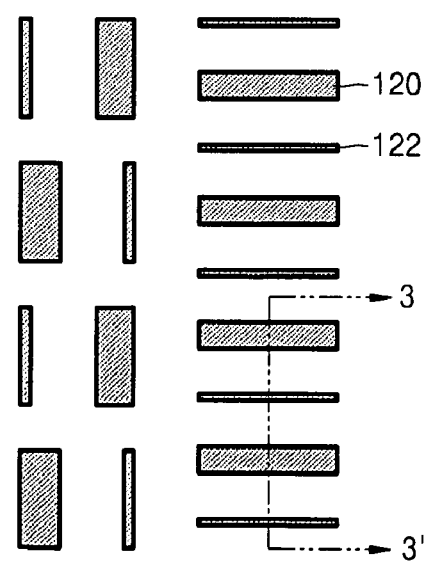
FIG. 2 is a top view of a portion of a DNA chip manufactured according to an embodiment of the present invention.

FIG. 2 is a top view of a portion of a DNA chip including a biological CMOS as illustrated in FIG. 1, manufactured according to an embodiment of the present invention.

A reference numeral 120 represents a DNA probe attached to a gate electrode of an NMOS transistor, and a reference numeral 122 represents a DNA probe attached to a gate electrode of a PMOS transistor. Therefore, the DNA probe 120 corresponds to the second DNA probe 106 of FIG. 1, and the DNA probe 122 corresponds to the first DNA probe 104 of FIG. 1.

A method of manufacturing a DNA chip according to an embodiment of the present invention will now be described with reference to FIGS. 3 through 11, which are cross-sectional views taken along 3-3' in FIG. 2. The main feature of the DNA chip manufacturing method illustrated in FIG. 1 lies in the processes after the formation of the third inter-layer insulation layer 100, during the selective formation of the organic layer 102 and the first and second DNA probes 104 and 106 respectively on the first gate electrode 40 and the second gate electrode 48 after the first contact hole H1 and the second contact hole H2 are formed in the first to third inter-layer insulation layers 54, 82 and 100. Hereinafter, the selective formation of the organic layer 102 and the first and second DNA probes 104 and 106 is referred to as a "first operation." FIGS. 3 through 11 illustrate the main elements related to the first operation, and elements that are not directly related to the first operation are not illustrated.

Figure 3:
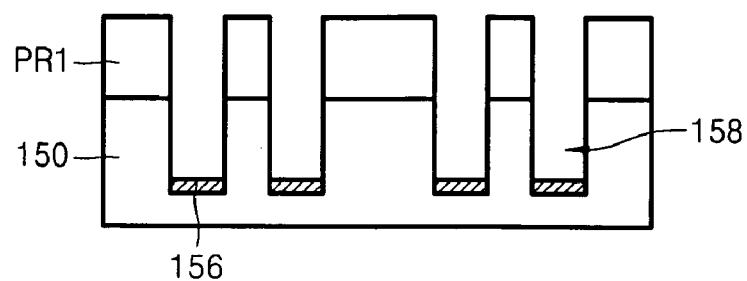
FIGS. 3 through 11 are cross-sectional views illustrating a method of manufacturing a DNA chip according to an embodiment of the present invention.

Referring to FIG. 3, a photoresist pattern PR1 is formed on an inter-layer insulation layer 150 to expose portions of the inter-layer insulation layer 150 formed on gate electrodes 156. Using the photoresist pattern PR1 as an etch mask, the exposed portions of the inter-layer insulation layer 150 are etched until the gate electrodes 156 are exposed. As a result, contact holes 158 exposing the gate electrodes 156 are formed in the inter-layer insulation layer 150. The inter-layer insulation layer 150 can be a stack structure including the first to third inter-layer insulation layers 54, 82 and 100 in sequential order as illustrated in FIG. 1. The gate electrodes 156 can be the first gate electrode 40 and the second gate electrode 48 illustrated in FIG. 1. Also, the contact holes 158 can be the first contact hole H1 and the second contact hole H1 illustrated in FIG. 1.

Figure 4:
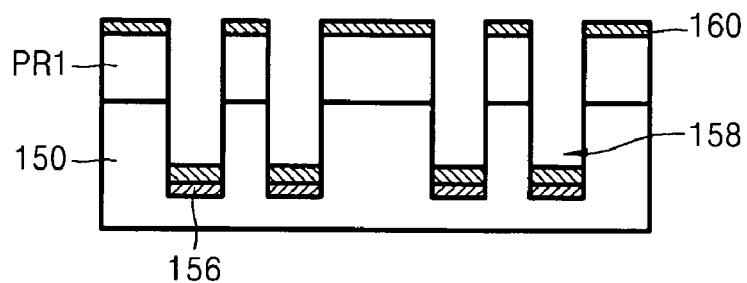
Figure 5:
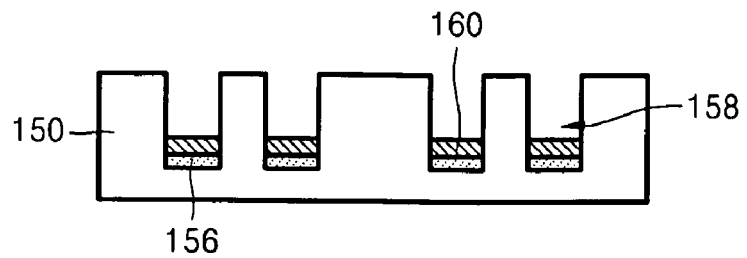

Referring to FIG. 4, using a deposition method, such as chemical vapor deposition (CVD), organic layers 160 are selectively formed on the photoresist pattern PR1 and the gate electrodes 156, which are exposed by the contact holes 158. The organic layers 160 are glue layers on which DNA probes are to be formed in a subsequent process. The organic layers 160 can be GAPS layers. After the formation of the organic layers 160, the photoresist pattern PR1 is removed, along with the organic layers 160 formed on the photoresist pattern PR1. Therefore, as illustrated in FIG. 5, the organic layers 160 remain on the gate electrodes 156 because the organic layers 160 are selectively formed on the upper surface of the gate electrodes 156.

Figure 6:
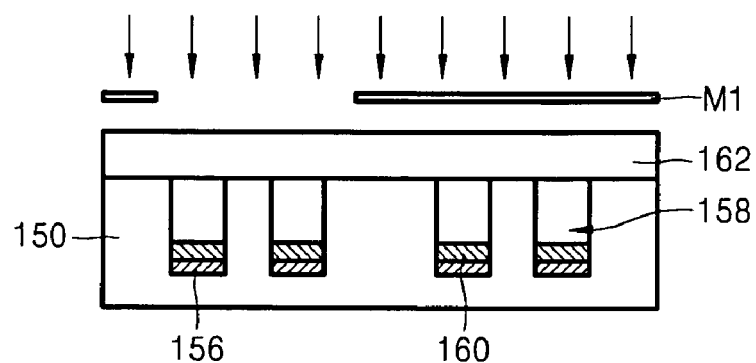
Figure 7:
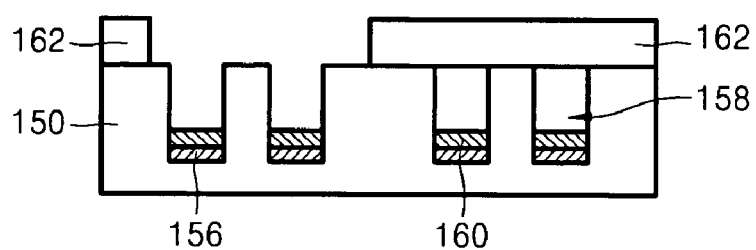

Referring to FIG. 6, a first photosensitive dry film resist (DFR) layer 162 is attached to the upper surface of the inter-layer insulation layer 150. A photo-mask M1 masking a portion of the organic layers 160 is aligned above the first DFR layer 162 and photo-exposed such that the portion of the first DFR layer 162 that is not masked by the photo-mask M1 is photo-exposed. The photo-mask M1 is removed and developed to remove the photo-exposed portion of the first DFR layer 162. As illustrated in FIG. 7, a portion of the organic layers 160 is exposed and the rest of the organic layers 160 is covered with the remaining portion of the first DFR layer 162. During the developing process applied to the first DFR layer 162, the organic layers 160 and DNA probes must not be damaged by a developing solution. Thus, the photo-exposed portion of the first DFR layer 162 can be developed by a developing solution that does not damage the organic layers 160 or the DNA probes. The developing solution can be a mild buffer solution including 1% $Na_2CO_3$. The photo-exposed portion of the first DFR layer 162 can be removed using an organic solution or a weak base solution.

Figure 8:
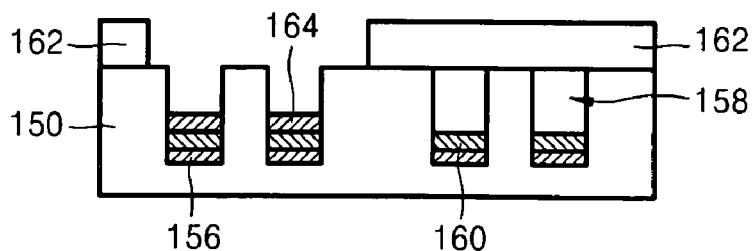

Referring to FIG. 8, the above resulting structure illustrated in FIG. 7 is immersed in a solution including a base included in a first DNA probe 164 and then cleaned, so that the first DNA probe 164 is attached to the exposed organic layers 160. The first DNA probe 164 can be the first DNA probe 104 of FIG. 1. After attaching the first DNA probe 164, the remaining portion of the first DFR layer 162 is removed by performing a strip process. The strip process can use a base solution or a weak base solution.

Figure 9:
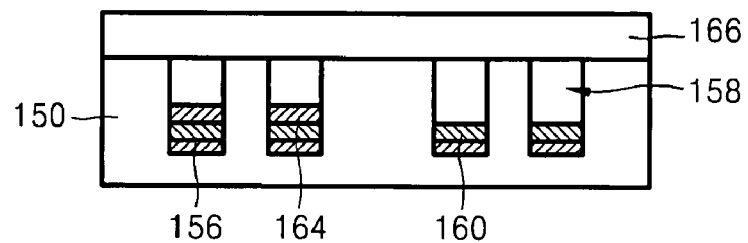
Figure 10:
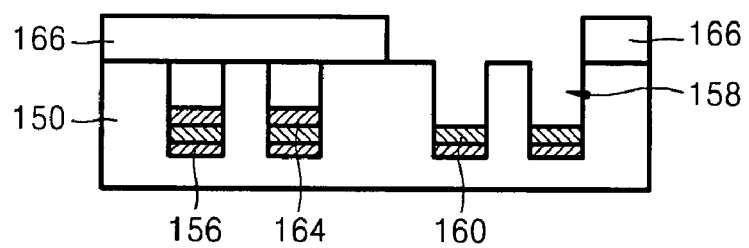

Referring to FIG. 9, a second DFR layer 166 is formed on the inter-layer insulation layer 150, covering the contact holes 158. As in the photo-exposure process for the first DFR layer 162, a portion of the second DFR layer 166 is photo-exposed and removed by a developing solution to thereby expose a portion of the organic layers 160 on which the first DNA probe 164 is not attached. FIG. 10 illustrates the second DFR layer 166 remaining after the developing process.

Figure 11:
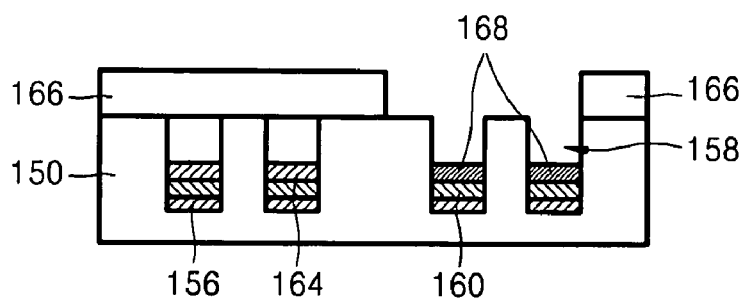

Referring to FIG. 11, a second DNA probe 168 is attached to the exposed portion of the organic layers 160. The second DNA probe 168 can be attached using the same operation as for attaching the first DNA probe 164. The first DNA probe 164 and the second DNA probe 168 can have different target DNA structures in a subsequent hybridization reaction. After attaching the second DNA probe 168, the remaining second DFR layer 166 is removed by a strip process.

A detailed description of an experiment which was performed to verify the excellence of the DNA chip manufacturing method according to the embodiment of the present invention will now be provided.

A DNA chip was manufactured according to the present embodiment as illustrated in FIGS. 3 through 11, and another DNA chip was manufactured by the same method except that a conventional photoresist layer was used instead of a DFR layer, to compare the conventional method with that of the present invention. A solution of approximately 2.38% tetramethyl ammonium hydroxide (TMAH) was used as a developing solution for the photoresist layer.

The parameters for comparison were the self-emission intensity and the FITC fluorescence intensity. Hereinafter, the DNA chip manufacturing method according to the present embodiment is referred to as a "first method," and the conventional DNA chip manufacturing method using a photoresist layer instead of a DFR layer as a "second method." In the first method, the self-emission intensity of the organic layer measured after the DFR layer was formed on the organic layer (e.g. the GAPS layer) and removed thereafter was approximately 620. In the second method, the self-emission intensity of the organic layer measured after the conventional photoresist layer was formed on the organic layer and removed thereafter was approximately 1,160. The self-emission intensity of an organic layer where neither the DFR layer or the conventional photoresist layer was formed (hereinafter referred to as a "pure organic layer") was approximately 618. These results show that the self-emission intensity of the first method was almost equal to that of the pure organic layer, whereas the self-emission intensity of the second method was nearly twice the self-emission intensity of the first method. This measurement result indicates that the DFR layer was almost completely removed from the upper surface of the organic layer in the first method. The same results were obtained for the FITC fluorescence intensity.

In the first method, the FITC fluorescence intensity of the organic layer, measured after the DFR layer was formed on the organic layer and removed thereafter, was approximately 7,220. In the second method, the FITC fluorescence intensity of the organic layer, measured after the conventional photoresist layer was formed on the organic layer and removed thereafter, was approximately 5,440. The FITC fluorescence intensity of the pure organic layer was approximately 7,040. These results show that the FITC fluorescence intensity of the first method was nearly equal to that of the pure organic layer, whereas the FITC fluorescence intensity of the second method was approximately 20% lower than that of the first method. Considering that the FITC fluorescence intensities of the first method and the pure organic layer were nearly the same, the reason for the low FITC fluorescence intensity of the second method was that the photoresist layer partially remained on the organic layer even after removal. This measurement result indicates that when the conventional photoresist layer was used as a photosensitive layer for the organic layer, the activation of the organic layer was decreased by approximately 20%, whereas the activation of the organic layer was barely changed when the DFR layer was used.

The above measurement results of the FITC fluorescence intensity were obtained when the DFR layer and the conventional photoresist layer were used once each in the first method and the second method. Hence, if the DFR layer and the conventional photoresist layer were used more than two times each in the first method and the second method, the difference between the first method and the second method would be more pronounced. Considering that the difference in the FITC fluorescence intensity between the first method and the second method was approximately 20% when using the DFR layer and the conventional photoresist layer once, and the difference indicated that the conventional photoresist layer partially remained on the organic layer, when the conventional photoresist layer was formed again on the organic layer, the removal rate of the conventional photoresist layer would become even lower than the previous one due to the remaining conventional photoresist layer. As a result, the activation level of the organic layer would be decreased by more than 20%. Theoretically, the activation level could be decreased by approximately 40%, which was about twice the activation level given when the conventional photoresist layer was coated one time.

Also, the fluorescence intensity after hybridization in the first method and the second method (i.e. the fluorescence intensity after the DNA probe is attached to the organic layer) was measured. With reference to FIGS. 3 through 11, after the formation of the organic layers 160 and before attaching the first DNA probe 164, the two organic layers 160 on the left were covered once with the first DFR layer 162 according to the first method or with the conventional photoresist layer according to the second method. In the first method, the organic layers 160 were not in contact with the first DFR layer 162. However, the two organic layers 160 on the right were covered twice with a DFR layer, the first was the first DFR layer 162 and the second was the second DFR layer 166, or twice with the conventional photoresist layer before attaching the second DNA probe 168.

Figure 12:
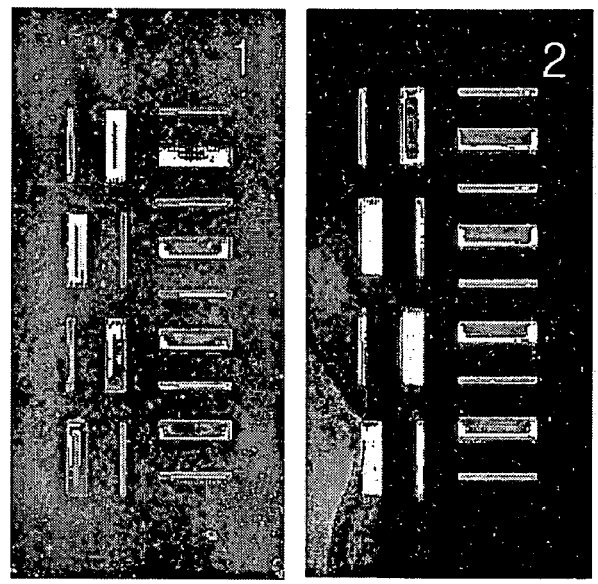
FIG. 12 is micrographic images showing a fluorescence intensity level measured after hybridization on a DNA chip manufactured according to an embodiment of the present invention.
Figure 13:
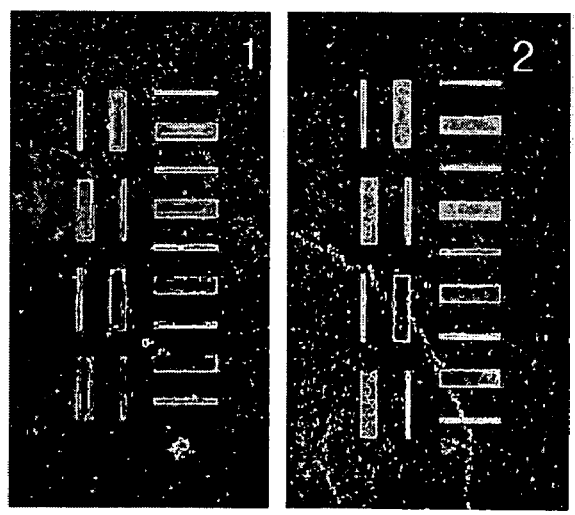
FIG. 13 is micrographic images showing a fluorescence intensity measured after hybridization on a DNA chip manufactured using a photoresist layer employed in a conventional semiconductor fabrication process.

FIGS. 12 and 13 are micrographic images showing a fluorescence intensity measured after the hybridization according to the first method and the second method. In FIG. 12, the micrographic image on the left illustrates the measurement result when the organic layer was covered once with the DFR layer, whereas the micrographic image on the right illustrates the measurement result when the organic layer was covered twice with the DFR layer. Similarly, in FIG. 13, the micrographic image on the left illustrates the measurement result when the organic layer was covered once with the conventional photoresist layer, whereas the micrographic image on the right illustrates the measurement result when the organic layer was covered twice with the conventional photoresist layer.

Comparing the two micrographic images of FIG. 12, in the first method, the measured fluorescence intensity was the same regardless of whether the organic layer was covered once or twice with the DFR layer. On the other hand, comparing the two micrographic images of FIG. 13, in the second method, the fluorescence intensity decreased greatly when the organic layer was covered twice with the conventional photoresist layer. This measurement result indicates that the activation level of the organic layer is decreased by a greater extent as the number of coated conventional photoresist layers increases.

The numerals 1 and 2 in FIG. 12 represent the number of coatings of the DFR layer, and the numerals 1 and 2 expressed in FIG. 13 represent the number of coatings of the conventional photoresist layer.

According to the exemplary embodiments of the present invention, a DFR layer is used as a photoresist layer when target surfaces are flat and gate electrodes are lower than the target surfaces. Thus, organic layers and DNA probes are not allowed to make direct contact with the DFR layer. Also, conventional photolithography can be used without any variation. Hence, an additional apparatus is not necessary. Since the organic layers and the DNA probes do not directly contact the DFR layer, the DFR layer can be removed completely from the organic layers and the DNA probes during a developing process. As a result, degradation of the activation level of the organic layer and DNA probes can be avoided.

While the present invention has been particularly shown and described with reference to exemplary embodiments thereof, it will be understood by those of ordinary skill in the art that various changes in form and detail may be made therein without departing from the spirit and scope of the present invention as defined by the following claims. For instance, the field effect transistors can be replaced with other types of transistors, and source electrodes and drain electrodes can be directly connected to source regions and drain regions without forming pad layers. Also, various other types of photo-exposure light for the DFR layer or developing solutions for the developing process can be used.

What is claimed is:

1. A method of manufacturing a DNA (deoxyribonucleic acid) chip having a plurality of transistors formed on a substrate and an organic layer and a DNA probe sequentially stacked on a gate of the transistor, the method comprising:

forming an inter-layer insulation layer on the substrate to cover the transistors, and planarizing the inter-layer insulation layer;

forming at least two contact holes exposing gate electrodes of the transistors, in the inter-layer insulation layer;

selectively forming organic layers directly on the exposed gate electrodes;

attaching a first DFR (dry film resist) layer to the upper surface of the inter-layer insulation layer to cover the contact holes;

removing a portion of the first DFR layer covering a first contact hole among the contact holes;

attaching a first DNA probe directly to the organic layer in the first contact hole; and removing a remaining portion of the first DFR layer.

2. The method of claim 1, further comprising:
forming a second DFR layer on the inter-layer insulation layer covering the contact holes;
removing a portion of the second DFR layer covering a second contact hole among the contact holes;
attaching a second DNA probe to the organic layer in the second contact hole; and
removing a remaining portion of the second DFR layer.

3. The method of claim 1, wherein the forming of the contact holes and the selectively forming of the organic layers on the gate electrodes further include:
forming a photoresist pattern on the inter-layer insulation layer, the photoresist pattern defining regions where the gate electrodes are formed;
etching the inter-layer insulation layer using the photoresist pattern as an etch mask until the gate electrodes are exposed;
forming the organic layers on the photoresist pattern and the gate electrodes; and
removing the photoresist pattern and the organic layer formed on the photoresist pattern.

4. The method of claim 1, wherein the organic layers are GammaAminoPropyltriethoxySilane (GAPS) layers.

5. The method of claim 1, wherein the portion of the first DFR layer is removed using a developing solution that does not damage the organic layers.

6. The method of claim 5, wherein the developing solution is a mild buffer solution.

7. The method of claim 1, wherein the remaining portion of the first DFR layer is removed by stripping using an organic solution or under a weak base condition.

* * * * *